(12) United States Patent
Hancock et al.

(10) Patent No.: US 11,678,931 B2
(45) Date of Patent: Jun. 20, 2023

(54) ELECTROSURGICAL PROBE FOR DELIVERING RF AND MICROWAVE ENERGY

(71) Applicant: CREO MEDICAL LIMITED, Chepstow (GB)

(72) Inventors: Christopher Paul Hancock, Bath (GB); Patrick Burn, Chepstow (GB); Pallav Shah, London (GB)

(73) Assignee: CREO MEDICAL LIMITED, Chepstow (GB)

( * ) Notice: Subject to any disclaimer, the term of this patent is extended or adjusted under 35 U.S.C. 154(b) by 946 days.

(21) Appl. No.: 16/072,845

(22) PCT Filed: Apr. 3, 2017

(86) PCT No.: PCT/EP2017/057864
§ 371 (c)(1),
(2) Date: Jul. 25, 2018

(87) PCT Pub. No.: WO2017/174513
PCT Pub. Date: Oct. 12, 2017

(65) Prior Publication Data
US 2019/0029751 A1    Jan. 31, 2019

(30) Foreign Application Priority Data

Apr. 4, 2016 (GB) ...................... 1605764

(51) Int. Cl.
*A61B 10/06* (2006.01)
*A61B 18/14* (2006.01)
(Continued)

(52) U.S. Cl.
CPC .......... *A61B 18/1492* (2013.01); *A61B 1/018* (2013.01); *A61B 1/2676* (2013.01);
(Continued)

(58) Field of Classification Search
CPC . A61B 18/1492; A61B 18/12; A61B 18/1815; A61B 34/20; A61B 1/018;
(Continued)

(56) References Cited

U.S. PATENT DOCUMENTS

| 5,026,959 A | 6/1991 | Ito et al. |
| 2005/0245919 A1 | 11/2005 | Van Der Welde |

(Continued)

FOREIGN PATENT DOCUMENTS

| EP | 2 868 340 A1 | 5/2015 | |
| GB | 2487199 A * | 7/2012 | ............. H01Q 21/06 |

(Continued)

OTHER PUBLICATIONS

The First Office Action, from the State Intellectual Property Office of People's Republic of China in counterpart Application No. 201780007874.1, dated Jul. 3, 2020.

(Continued)

*Primary Examiner* — Linda C Dvorak
*Assistant Examiner* — Ryan T Clark
(74) *Attorney, Agent, or Firm* — ArentFox Schiff LLP (57) ABSTRACT

An energy delivery system for performing tissue ablation at the distal end of an Electromagnetic Navigation Bronchoscopy (ENB) instrument. The system is insertable through an instrument channel of a steerable instrument cord in an ENB instrument, and comprise a coaxial cable with a radiating tip portion. The tip portion comprises a first conductive element electrically connected to the coaxial cable's inner conductor and a second conductive element electrically isolated from the inner conductor. The conductive elements are arranged to act as: an active electrode and a return electrode for delivering the RF energy into tissue surrounding the radiating tip portion, and an antenna for radiating the microwave energy as a localized microwave field. The system may be (Continued)

arranged to delivery energy according to a predetermined profile comprising interleaving periods of RF and microwave energy or a combination thereof, or a dynamic profile based on detected tissue impedance.

13 Claims, 5 Drawing Sheets
(1 of 5 Drawing Sheet(s) Filed in Color)

(51) Int. Cl.
    *A61B 18/18*      (2006.01)
    *A61B 18/12*      (2006.01)
    *A61B 34/20*      (2016.01)
    *A61B 1/018*      (2006.01)
    *A61B 1/267*      (2006.01)
    *A61B 10/04*      (2006.01)
    *A61B 17/00*      (2006.01)
    *A61B 18/00*      (2006.01)

(52) U.S. Cl.
    CPC .............. *A61B 10/04* (2013.01); *A61B 10/06* (2013.01); *A61B 18/12* (2013.01); *A61B 18/1206* (2013.01); *A61B 18/1815* (2013.01); *A61B 34/20* (2016.02); *A61B 2017/0034* (2013.01); *A61B 2017/00084* (2013.01); *A61B 2017/00154* (2013.01); *A61B 2017/00809* (2013.01); *A61B 2018/00178* (2013.01); *A61B 2018/00541* (2013.01); *A61B 2018/00577* (2013.01); *A61B 2018/00642* (2013.01); *A61B 2018/00702* (2013.01); *A61B 2018/00708* (2013.01); *A61B 2018/00821* (2013.01); *A61B 2018/00875* (2013.01); *A61B 2018/00982* (2013.01); *A61B 2018/00994* (2013.01); *A61B 2018/183* (2013.01); *A61B 2018/1823* (2013.01); *A61B 2018/1861* (2013.01); *A61B 2034/2051* (2016.02)

(58) Field of Classification Search
    CPC ... A61B 1/2676; A61B 10/04; A61B 18/1206; A61B 2018/00541; A61B 2018/00708; A61B 2017/00154
    See application file for complete search history.

(56) References Cited

U.S. PATENT DOCUMENTS

| 2006/0282069 | A1 | 12/2006 | Prakash et al. |
| 2006/0289528 | A1* | 12/2006 | Chiu ..................... A61B 18/18 219/748 |
| 2007/0198006 | A1* | 8/2007 | Prakash ................. A61B 18/18 606/33 |
| 2008/0167639 | A1* | 7/2008 | Gilboa ................... A61B 5/062 604/514 |
| 2009/0306644 | A1 | 12/2009 | Mayse et al. |
| 2010/0286687 | A1* | 11/2010 | Feldberg ............ A61B 18/1815 606/33 |
| 2010/0298822 | A1* | 11/2010 | Behnke ................. A61B 18/18 606/33 |
| 2013/0116679 | A1 | 5/2013 | Van Der Weide et al. |
| 2013/0237977 | A1 | 9/2013 | McCarthy et al. |
| 2013/0267943 | A1 | 10/2013 | Hancock |
| 2013/0274733 | A1* | 10/2013 | Hancock ............ A61B 18/1445 606/33 |
| 2013/0289557 | A1* | 10/2013 | Hancock ............ A61B 18/1815 606/33 |
| 2013/0324995 | A1 | 12/2013 | Dresher |
| 2014/0046174 | A1 | 2/2014 | Ladtkow et al. |
| 2015/0196353 | A1 | 7/2015 | Hancock et al. |
| 2015/0272671 | A1 | 10/2015 | Van Der Weide et al. |
| 2015/0322759 | A1* | 11/2015 | Okoniewski ........ E21B 43/2401 166/60 |
| 2016/0074091 | A1 | 3/2016 | Amoah et al. |
| 2021/0068897 | A1* | 3/2021 | Wong ...................... H05B 6/72 |

FOREIGN PATENT DOCUMENTS

| WO | WO 2014/184544 A1 | 11/2014 |
| WO | WO 2015/066311 A1 | 5/2015 |
| WO | WO 2015/097446 A1 | 7/2015 |
| WO | WO 2015/097472 A1 | 7/2015 |

OTHER PUBLICATIONS

British Search Report dated Aug. 31, 2016 issued in British Application No. GB1605764.8.
International Search Report and Written Opinion dated Jun. 7, 2017 issued in International Application No. PCT/EP2017/057864.

* cited by examiner

ELECTROSURGICAL PROBE FOR DELIVERING RF AND MICROWAVE ENERGY

CROSS-REFERENCE TO RELATED APPLICATIONS

This application is a 35 U.S.C. § 371 National Phase of PCT Application No. PCT/EP2017/057864 filed Apr. 3, 2017, which claims priority to British Application GB 1605764.8 filed Apr. 4, 2016. The disclosures of these prior applications are hereby incorporated by reference herein.

FIELD OF THE INVENTION

The invention relates to an electrosurgical probe for delivering radiofrequency and microwave energy to biological tissue in order to ablate the target tissue. In particular, the probe is configured to be insertable through a channel of a bronchoscope or catheter that can be steered into the lungs, e.g. to ablate tumours, lesions or fibroids and to treat asthma.

BACKGROUND TO THE INVENTION

It is inherently difficult to gain access to lung tumours due to the small dimensions of the bronchial tree, especially towards the peripheral regions where small nodules are likely to develop. This has resulted in many treatment options being employed such as chemotherapy (targeted medicine, anti-cancer drugs (chemotherapeutic agents)), radiotherapy (delivery of ionizing radiation), surgery (invasive and minimally invasive) and RF/microwave ablation. Surgical procedures involve pneumonectomy (removal of one lung), lobectomy (removal of a lobe), sleeve lobectomy (resection of a lobe along with part of the bronchus that attaches to it), wedge resection (removal of a wedge shaped portion of lung) and segmentectomy/segment resection (resection of a specific lung segment).

It is known to use microwave emitting probes to treat various conditions in the lungs and other body tissues. For example, in the lungs, microwave radiation can be used to treat asthma and ablate tumours or lesions.

Existing microwave ablation devices on the market are designed to be inserted percutaneously. However, such devices are difficult to locate percutaneously into a moving lung, which can lead to complications such as pneumothorax and haemothorax (air and blood within the pleural cavity respectively).

Using a probe to deliver the energy to target tissue is preferable because the radiating portion can be positioned close to the target site and so a high proportion of power can be transmitted to the target site and a lower proportion is lost to the surrounding healthy tissue. This reduces side effects of treatment as well as increasing efficiency.

Efficient lung cancer treatment through minimally invasive procedures is desirable to reduce the mortality rate of lung cancer patients and to reduce the intraoperative and postoperative complication rate. Probes can be inserted into tissue via laparoscopic surgery, open surgery or via channels in the body such as airways. The least invasive method is the use of channels in the body and this reduces strain put on a patient by the procedure. Catheters or bronchoscopes can be used to help to guide the instrument to the target site and some examples of the mechanisms used are given in US2009/306644.

In US2014/046174, a microwave ablation catheter is disclosed with a radiating section that is delivered to the target site by a bronchoscope through the airways of a patient.

Various designs of radiating portions can be used, such as a coaxial cable with a radiating portion on the distal end as in US2014/046174 and the energy delivery device of US2013/324995.

SUMMARY OF THE INVENTION

At its most general, the invention provides an energy delivery system that can enable ablation to be performed at the distal end of an Electromagnetic Navigation Bronchoscopy (ENB) instrument. ENB systems are capable of accessing tumours that are beyond the reach of conventional bronchoscopes, but are typically used for location marking and biopsy processes. For example, the ENB catheter is normally navigated into the airways using the imaging system and then a biopsy tool is introduced to take a tissue biopsy once the clinician knows the location of the tissue mass so that there is a high degree of confidence that the biopsy is a nodule or tumour mass.

Electrosurgical treatment, especially tissue ablation, is challenging in this environment because of the difficulty in delivering sufficient power through the narrow diameter available in the instrument without consequential losses causing unwanted effects, e.g. due to the instrument becoming too hot along its length.

Energy loss is a problem because the space available for conveying the energy is small. The instrument channel of a typical ENB instrument cord or catheter is typically equal to or less than 2.0 mm.

The disclosure herein presents a number of coaxial-based energy delivery configurations, e.g. coaxial cable with distal radiating portion, that can use a combination of RF and microwave in a way that achieves a desired ablation effect while minimises or eliminating unwanted effects caused by energy losses. Thus, the invention may provide a tissue ablation instrument capable of being introduced into the guide catheter of an ENB apparatus, so that it can be steered through the complex airways within the lung (i.e. into the bronchial tree and to the bronchioles).

The tissue ablation instrument may comprise a coaxial cable and a distal end assembly that both have a maximum out diameter equal to or less than 1.9 mm, ideally 1.6 mm or less, or even 1.5 mm or less. This geometry can fit into an ENB catheter once the nodule or mass has been located to ablate a tissue mass. A possible procedure may comprise: (i) introduce ENB catheter, (ii) take biopsy sample, (iii) assess sample histology immediately (while catheter remains in place), and (iv) if treatment is needed, introduce tissue ablation antenna and perform ablation. Another possible procedure would be to ablate whenever a nodule is identified, i.e. ablate irrespective of whether the nodule is non-cancerous or cancerous.

Also disclosed herein are a number of RF/microwave energy delivery profiles that can be used with the invention, i.e. which are designed to minimise or eliminate energy losses while provide enough energy to achieve tissue ablation. The energy delivery profiles may be based on detected tissue impedance or (e.g. in the absence of tissue impedance information) may comprise predetermined (i.e. fixed in advance) patterns of energy delivery, e.g. comprising interleaving periods of RF and microwave energy or a combination of the two.

In this specification "microwave" may be used broadly to indicate a frequency range of 400 MHz to 100 GHz, but preferably the range 1 GHz to 60 GHz. Specific frequencies that have been considered are: 915 MHz, 2.45 GHz, 3.3 GHz, 5.8 GHz, 10 GHz, 14.5 GHz and 24 GHz. The device may delivery energy at more than one of these microwave frequencies. In contrast, this specification uses "radiofrequency" or "RF" to indicate a frequency range that is at least three orders of magnitude lower, e.g. up to 300 MHz, preferably 10 kHz to 1 MHz.

According to the invention, there is provided an electrosurgical apparatus for delivering radiofrequency (RF) energy and microwave energy into lung tissue, the electrosurgical apparatus comprising: a generator for generating RF energy and microwave energy separately or simultaneously; an electrosurgical instrument comprising: a coaxial cable connected to the generator and arranged to convey RF energy and microwave energy, the coaxial cable having an inner conductor, an outer conductor, and a dielectric material separating the inner conductor and outer conductor; and a radiating tip portion disposed at a distal end of the coaxial cable to receive the RF energy and microwave energy from the coaxial cable, wherein the radiating tip portion comprise a first conductive element electrically connected to the inner conductor and a second conductive element electrically isolated from the inner conductor, wherein the first conductive element and the second conductive element are arranged to act as: an active electrode and a return electrode for delivering the RF energy into tissue surrounding the radiating tip portion, and an antenna for radiating the microwave energy as a localized microwave field, and wherein the electrosurgical instrument is insertable through an instrument channel of a steerable instrument cord in an electromagnetic navigation bronchoscope. The invention thus provides an electrosurgical instrument that is dimensioned to fit with an ENB catheter and capable of delivering both RF energy and microwave energy to biological tissue. A single instrument can therefore be used to deliver a desired amount of power using a suitable delivery medium (e.g. RF or microwave depending on the impedance of the tissue), which can achieve tissue ablation in regions of the lung where minimally invasive ablation treatment was previously impossible.

The apparatus of the invention may include an electromagnetic navigation bronchoscope having a steerable instrument cord for non-percutaneous insertion into a patient's lungs, the instrument cord having an instrument channel running along its length.

In order to be maneuverable and to access the distal end of the instrument cord, the coaxial cable and the radiating tip portion may have a maximum outer diameter equal to or less than 1.9 mm, preferably equal to or less than 1.6 mm.

The components that convey the microwave energy may be designed to minimise loss as far as possible. For example, the coaxial cable may be arranged to exhibit a loss of 2 dB/m or less when conveying the microwave energy, e.g. through suitable choice or materials and geometry.

The manner in which energy is delivered from the generator to the instrument may also affect the effect of the losses. The generator may thus be arranged to deliver RF energy and microwave energy to cause tissue ablation at the radiating tip portion according to an energy delivery profile. The energy delivery profile may be a data structure that specifies the magnitude, duration and other parameters of the RF energy and microwave energy to ensure that a desired amount or power or energy is delivered into tissue or to ensure that a certain tissue effect (e.g. ablation within a certain volume) is achieved.

The energy delivery profile may comprise an initial portion consisting solely of RF energy. At the beginning of treatment, tissue has an impedance that makes it susceptible to RF heating. An initial volume of ablation can be achieved using RF energy. This is advantageous because the coaxial cable may exhibit negligible losses at frequencies corresponding to the RF energy.

The energy delivery profile may comprise a microwave ablation portion comprising pulsed microwave energy, e.g. where the microwave energy comprises a series of ON portions in which the microwave energy is delivered separated by a series of OFF portions where the microwave energy is not delivered. During the OFF portions the loss from the cable is negligible, which can give time for the lost energy (heat) to dissipate. RF energy may be delivered in one or more of the OFF portions to maintain the ablation volume.

The generator may be arranged to detect the impedance of tissue at the radiating tip portion. The energy delivery profile may be adjustable based on the detected impedance. For example, the energy delivery profile may comprise a first portion consisting solely of RF energy followed by a second portion comprising microwave energy. The generator may be arranged to switch to the second portion when the tissue impedance is determined to exceed a predetermined threshold. However, it may not be necessary for the tissue impedance to be monitored. The energy delivery profile may have fixed parameters, e.g. duration, power level, etc.

The energy delivery profile may comprise a portion in which the microwave energy is delivered, the generator being arranged to modulate the microwave energy at a frequency corresponding to the RF energy. This may reduce the effect of the losses from the cable whilst maintaining the ablation effect at the distal end of the device.

The first conductive element may comprise a length of the inner conductor that extends beyond a distal end of the outer conductor, the first conductive element being surrounded along its length by the dielectric material. This structure forms a dipole antenna for the microwave energy. The second conductive element may be the distal end of the outer conductor, and can form the return electrode for the RF energy.

The first conductive element and the second conductive element may form one or more circumferential radiating slots in the radiating tip portion. Each slot may be a strip of removed outer conductor, where the dielectric material is exposed. The outer conductor may be removed around all or part of the circumference. In order to provide a spherical-type ablation volume, it is preferred for the slot to be around the whole circumference.

In one example, the first conductive element and the second conductive element may form a plurality of circumferential radiating slots in the radiating tip portion, the plurality of radiating slots including a proximal slot having a length of about one tenth of a wavelength of the microwave energy in the dielectric material, a distal slot having a length of about one tenth of a wavelength of the microwave energy in the dielectric material, and an intermediate slot between the proximal slot and the distal slot, the intermediate slot having a length of about one quarter of a wavelength of the microwave energy in the dielectric material. Other slot configurations can be used.

A radiating slot may be used in combination with a dipole type radiator. For example, the first conductive element may extend beyond a distal end of the second conductive portion in a distal region of the radiating tip portion. Alternatively, the first conductive element and the second conductive element may both extend beyond a distal edge of the slot to a distal face of the radiating tip portion.

The first conductive element may be exposed at the distal face of the radiating tip portion, e.g. to form the active electrode, and/or to form a radiating structure with the distal edge of the second conductive element.

The instrument may comprise a pair of jaws that can be opened and closed to collect a biopsy sample. The first conductive element and the second conductive element may be incorporated, e.g. part of or mounted on, the pair of jaws.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

Embodiments of the invention are discussed below with reference to the accompanying drawings, in which.

DETAILED DESCRIPTION; FURTHER OPTIONS AND PREFERENCES

Figure 1:
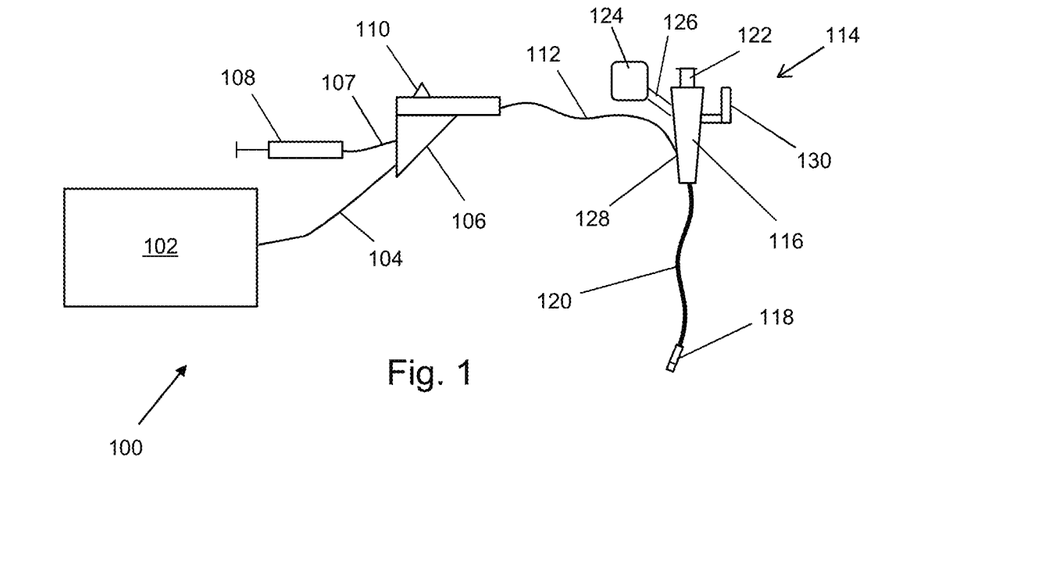
FIG. 1 is a schematic diagram showing a lung ablation system for use with an electromagnetic navigation bronchoscopy apparatus that is an embodiment of the invention.

FIG. 1 is a schematic diagram of a complete electrosurgery system 100 that is capable of supplying microwave energy and fluid, e.g. cooling fluid, to the distal end of an invasive electrosurgical instrument. The system 100 comprises a generator 102 for controllably supplying radiofrequency (RF) and microwave energy. A suitable generator for this purpose is described in WO 2012/076844, which is incorporated herein by reference. The generator may be arranged to monitor reflected signals received back from the instrument in order to determine an appropriate power level for delivery. For example, the generator may be arranged to calculate an impedance seen at the distal end of the instrument in order to determine an optimal delivery power level. The generator may be arranged to deliver power in a series of pulses which are modulated to match a patient's breathing cycle. This will allow for power delivery to occur when the lungs are deflated.

The generator 102 is connected to an interface joint 106 by an interface cable 104. The interface joint 106 is also connected to receive a fluid supply 107 from a fluid delivery device 108, such as a syringe. If needed, the interface joint 106 can house an instrument control mechanism that is operable by sliding a trigger 110, e.g. to control longitudinal (back and forth) movement of one or more control wires or push rods (not shown). If there is a plurality of control wires, there may be multiple sliding triggers on the interface joint to provide full control. The function of the interface joint 106 is to combine the inputs from the generator 102, fluid delivery device 108 and instrument control mechanism into a single flexible shaft 112, which extends from the distal end of the interface joint 106.

The flexible shaft 112 is insertable through the entire length of an instrument (working) channel of a bronchoscope 114, which in the present invention is preferably part of an electromagnetic navigation bronchoscopy (ENB) system, e.g. such as Covidien's SuperDimension® navigation system.

The bronchoscope 114 comprises a body 116 having a number of input ports and an output port from which an instrument cord 120 extends. The instrument cord 120 comprises an outer jacket which surrounds a plurality of lumens. The plurality of lumens convey various things from the body 116 to a distal end of the instrument cord 120. One of the plurality of lumens is the instrument channel discussed above. Other lumens may include a channel for conveying optical radiation, e.g. to provide illumination at the distal end or to gather images from the distal end. The body 116 may include a eye piece 122 for viewing the distal end. In order to provide illumination at the distal end, a light source 124 (e.g. LED or the like) may be connected to the body 116 by an illumination input port 126.

The flexible shaft 112 has a distal assembly 118 (not drawn to scale in FIG. 1) that is shaped to pass through the instrument channel of the bronchoscope 114 and protrude (e.g. inside the patient) at the distal end of the bronchoscope's tube. The distal end assembly includes an active tip for delivering radiofrequency and/or microwave energy into biological tissue.

The structure of the distal assembly 118 discussed below may be particularly designed for use with an ENB system, whereby the maximum outer diameter of the distal assembly 118 is equal to or less than 2.0 mm, e.g. less than 1.9 mm (and more preferably less than 1.5 mm) and the length of the flexible shaft can be equal to or greater than 1.2 m.

The body 116 includes a power input port 128 for connecting to the flexible shaft, which comprises a coaxial cable (e.g. a conventional coaxial cable) capable of conveying the radiofrequency and microwave energy from the generator 102 to the distal assembly 118. Coaxial cables that are physically capable of fitting down the instrument channel of a ENB device are available with the following outer diameters: 1.19 mm (0.047"), 1.35 mm (0.053"), 1.40 mm (0.055"), 1.60 mm (0.063"), 1.78 mm (0.070"). Custom-sized coaxial cables (i.e. made to order) may also be used.

As discussed above, it is desirable to be able to control the position of at least the distal end of the instrument cord 120. The body 116 may include a control actuator 130 that is mechanically coupled to the distal end of the instrument cord 120 by one or more control wires (not shown), which extend through the instrument cord 120. The control wires may travel within the instrument channel or within their own dedicated channels. The control actuator 130 may be a lever or rotatable knob, or any other known catheter manipulation device. The manipulation of the instrument cord 120 may be software-assisted, e.g. using a virtual three-dimensional map assembled from computer tomography (CT) images.

Figure 2:
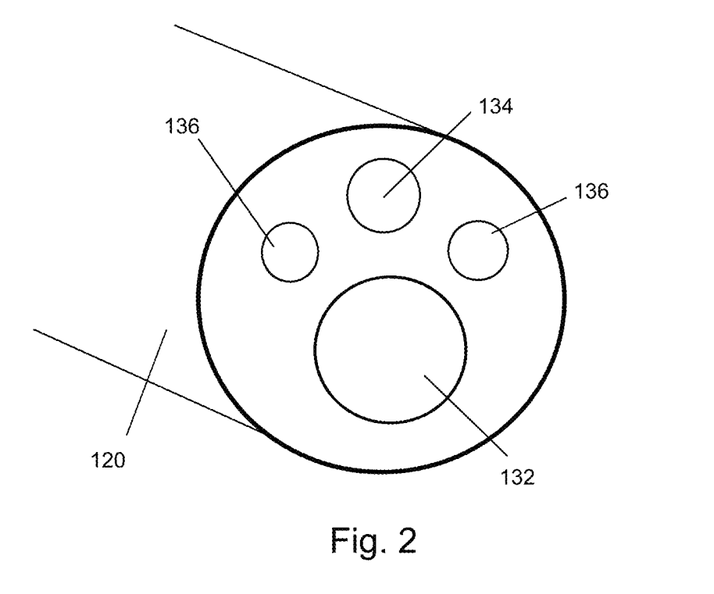
FIG. 2 is a schematic sectional view through an instrument cord of a bronchoscopy instrument that can be used with the present invention.

FIG. 2 is a view down the axis of the instrument cord 120. In this embodiment there are four lumens within the instrument cord 120. The largest lumen is the instrument channel 132. The other lumens comprise a camera channel 134 and a pair of illumination channels 136, but the invention is not limited to this configuration. For example, there may be other lumens, e.g. for control wires or fluid delivery or suction.

The invention seeks to provide an instrument that can perform tissue ablation at the distal end of an ENB system catheter. In order for side effects to be reduced and the efficiency of the instrument to be maximised, the transmitting antenna should be located as close to the target tissue as possible. Ideally, the radiating part of the instrument is located inside (e.g. at the centre of) the tumour during treatment. In order to reach the target site within the lungs, the instrument will need to be guided through the airways and around obstacles such as the vocal chords. This means that the instrument will ideally be flexible and have a small cross section. Particularly, the instrument should be very flexible near the antenna where it needs to be steered along bronchioles which can be narrow and winding. The size of the antenna part of the instrument should also be reduced where possible to allow the antenna to work properly in small locations and increase flexibility of the instrument when components of the antenna are rigid.

The description below presents a number of antenna configurations that are suitable for use in the distal assembly 118 described. Also disclosed are a number of energy delivery profiles. It is to be understood that any of the energy delivery profiles may be used with any of the antenna structures, and that all possible combinations are to be understood as being disclosed.

In the following description, unless stated otherwise, the length of a component refers to its dimension in the direction parallel to the longitudinal axis of the coaxial cable/instrument cord.

Figure 3:
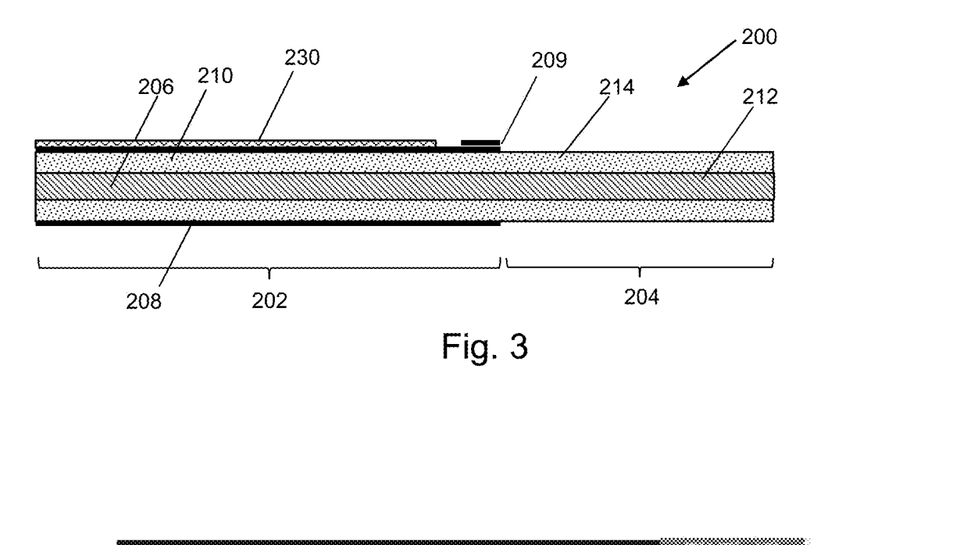
FIG. 3 is a cross-sectional view through an ablation instrument suitable for use in the present invention.

FIG. 3 is a cross-sectional view of the distal end of an electrosurgical instrument 200 that is used as the radiator in the distal assembly 118 in an embodiment of the invention. The electrosurgical instrument 200 comprises a coaxial cable 202 that is connected at its proximal end to a electrosurgical generator (not shown) in order to convey radiofrequency (RF) and microwave energy. The coaxial cable 202 comprises an inner conductor 206, which is separated from an outer conductor 208 by a first dielectric material 210. The coaxial cable 202 is preferably low loss for microwave energy. A choke (not shown) may be provided on the coaxial cable to inhibit back propagation of microwave energy reflected from the distal end and therefore limit backward heating along the device.

The device may include a temperature sensor at the distal end. For example, in FIG. 3 a thermocouple 230 is mounted on the outer conductor to transmit a signal back to the proximal end that is indicative of temperature at the distal end of the instrument.

Other techniques for temperature monitoring can be used. For example, one or more micromechanical structure whose physical configuration is sensitive to temperature may be mounted in the distal portion of the device, e.g. in or on the outer sheath discussed below. These structures can be interfaced with an optical fibre, whereby changes in a reflected signal caused by movement of the structure can be indicative of temperature changes.

The coaxial cable 202 terminates at its distal end with a radiating tip section 204. In this embodiment, the radiating tip section 204 comprises a distal conductive section 212 of the inner conductor 206 that extends before a distal end 209 of the outer conductor 208. The distal conductive section 212 is surrounded at its distal end by a dielectric tip 214 formed from a second dielectric material, which can be the same or different from the first dielectric material 210. The length of the dielectric tip 214 is shorter than the length of the distal conductive section 212.

The coaxial cable 202 and radiating tip section 204 may have a biocompatible outer sheath (not shown) formed over their outermost surfaces. The outer sheath 218 may be formed from a biocompatible material.

The dielectric tip 214 may have any suitable distal shape, e.g. any of dome shape, cylindrical, conical, etc. A smooth dome shape may be preferred because it increases the mobility of the antenna as it is maneuvered through small channels.

Figure 4:
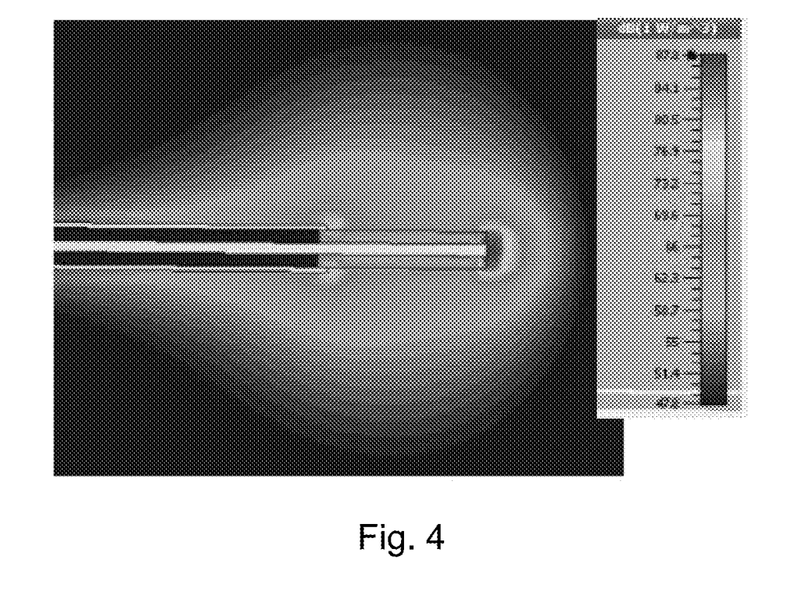
FIG. 4 is a diagram showing simulated power loss from the instrument of FIG. 3.

FIG. 4 shows a longitudinal cross section of a simulation of the absorption pattern of an antenna having the configuration shown in FIG. 3.

During treatment, the surrounding tissue absorbs the radiated energy. The volume of tissue into which the energy is delivered depends on the frequency of the microwave energy.

Figure 5:
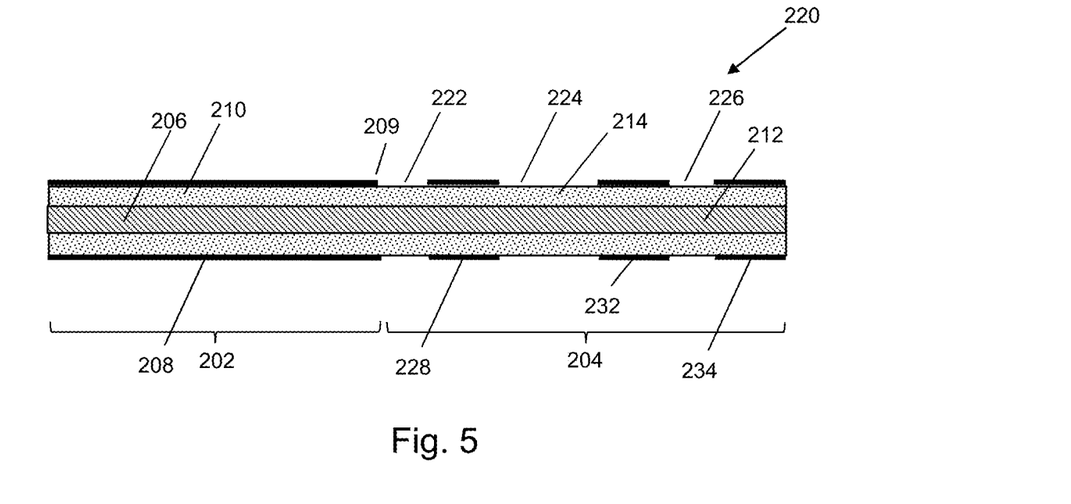
FIG. 5 is a cross-sectional view through another ablation instrument suitable for use in the present invention.

FIG. 5 is a cross-sectional view of the distal end of an electrosurgical instrument 220 that is used as the radiator in the distal assembly 118 in another embodiment of the invention. Features in common with FIG. 3 are given the same reference numbers and are not described again.

In FIG. 5, the radiating tip section 204 comprises a three-slot antenna formed by removing the outer conductor 208 from three circumferential regions 222, 224, 226 to leave three sections of exposed dielectric. The three circumferential regions (also referred to herein as "slots") 222, 224, 226 are separated by short coaxial sections 228, 232. The distalmost slot 226 is set back from the distal tip of the instrument 220, whereby the instrument terminates with a coaxial section 234. Proximal slot 222 and distal slot 226 have a length substantially equivalent to one tenth of a wavelength of the microwave energy within the dielectric material 214. The middle slot 224 has a length that is substantially equivalent to a quarter wavelength of the microwave energy within the dielectric material 214. The separation distances of the slots, i.e. the length of the coaxial sections 228, 232 and 234 is substantially equivalent to a quarter wavelength of the microwave energy within the dielectric material 214.

Figure 6:
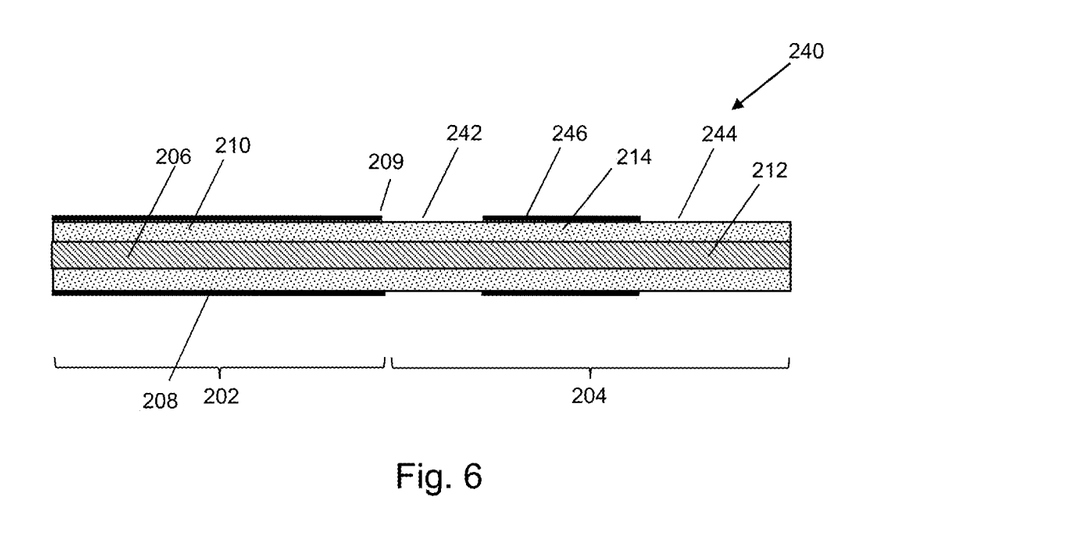
FIG. 6 is a cross-sectional view through another ablation instrument suitable for use in the present invention.

FIG. 6 is a cross-sectional view of the distal end of an electrosurgical instrument 240 that is used as the radiator in the distal assembly 118 in another embodiment of the invention. Features in common with FIG. 3 are given the same reference numbers and are not described again.

In FIG. 6, the radiating tip section 204 comprises a combined dipole and slot antenna. This is to make the power loss density profile more spherical and reduce backward heating down the external surface of the coaxial cable. A radiating slot 242 is formed by removing the outer conductor 208 from a circumferential region to expose the dielectric material. The slot 242 is separated by a short coaxial sections 246 from a distal tip section 244 in which the outer conductor is also removed. The distal tip section 244 functions in the same manner as the whole radiating tip section 204 of the embodiment shown in FIG. 3.

The slot 242 has a length substantially equal to one tenth of a wavelength of the microwave energy within the dielectric material 214. The separation distance between the slot 242 and the distal tip section 244 (i.e. the length of coaxial section 246) is substantially equal to a quarter wavelength of the microwave energy within the dielectric material 214.

Figure 7:
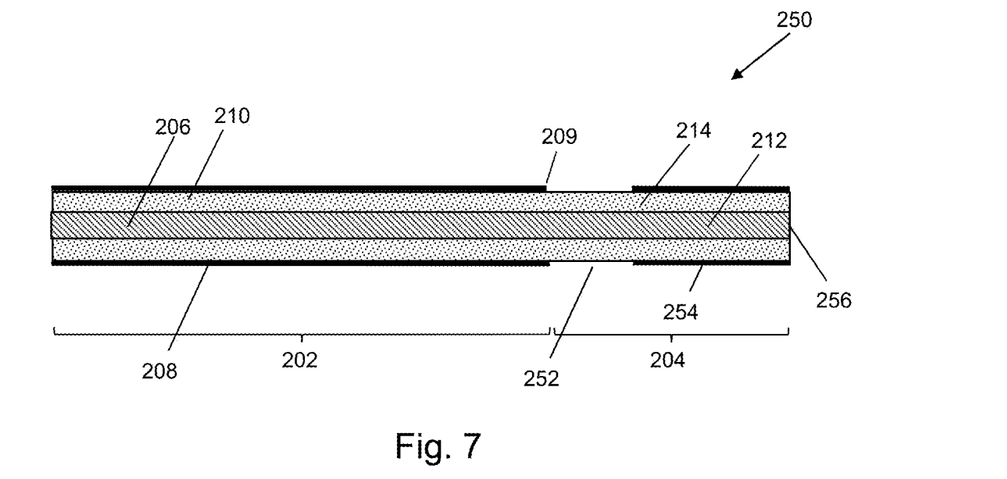
FIG. 7 is a cross-sectional view through another ablation instrument suitable for use in the present invention.

FIG. 7 is a cross-sectional view of the distal end of an electrosurgical instrument 250 that is used as the radiator in the distal assembly 118 in another embodiment of the invention. Features in common with FIG. 3 are given the same reference numbers and are not described again.

In FIG. 7, the radiating tip section 204 comprises a single slot antenna and a radiating distal end face. This configuration exhibits a non-spherical power loss density profile, which demonstrates that different shaped power loss density profiles can be produced by varying the geometry of the radiating tip section.

In FIG. 7, a radiating slot 252 is formed by removing the outer conductor 208 from a circumferential region to expose the dielectric material. The slot 252 is separated from the distal end face 256 of the instrument by a short coaxial sections 254, which terminates flush with the distal end face 256.

The ablation antenna of the invention may be incorporated into a biopsy tool. With this combination, the functions of tissue sampling and ablation may be provided by a single instrument, which may speed up the procedure.

Figure 8A:
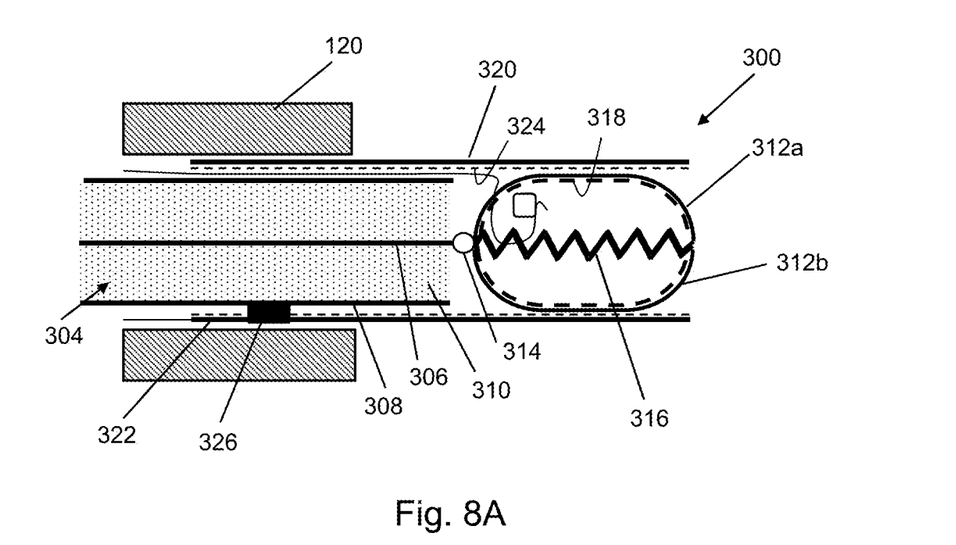
FIG. 8A is a cross-sectional view through a combined biopsy and ablation instrument suitable for use in the present invention when in a closed/retracted configuration.
Figure 8B:
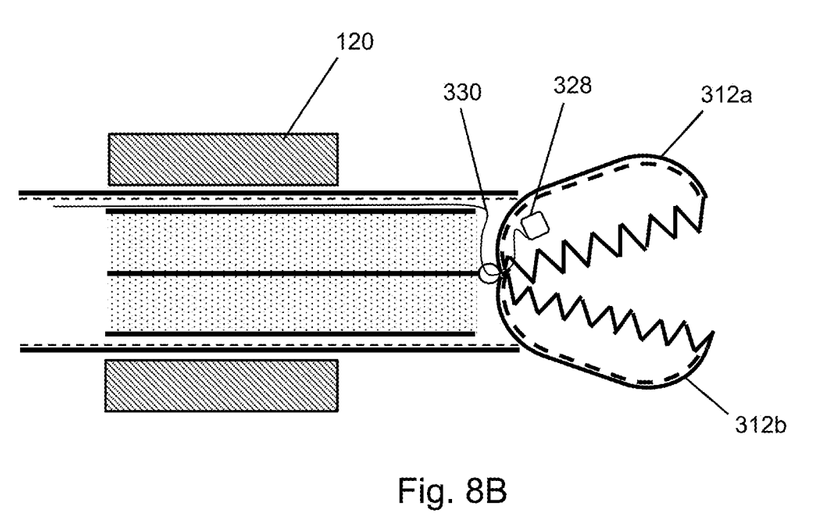
FIG. 8B is a cross-sectional view through the instrument of FIG. 8A when in an open/protruding configuration.

FIGS. 8A and 8B show an example of a combined biopsy and ablation instrument. FIG. 8A shows a schematic representation of a cross-sectional view of the distal jaw assembly 300 that can be used as the radiator in the distal assembly 118 in another embodiment of the invention. The distal jaw assembly 300 protrudes from a distal end of the instrument cord 120. A coaxial cable 304 conveyed by the instrument cord 120 comprises an inner conductor 306, an outer conductor 308 and a dielectric material 310 separating the inner conductor 306 from the outer conductor 308. At the distal end of the coaxial cable 304, a pair of jaws 312a, 312b is disposed. The pair of jaws 312a, 312b are pivotably connected to each other, e.g. by a hinge 314 at the proximal end of the pair of jaws 312a, 312b. The pair of jaws 312a, 312b form a shell that encloses a volume for collecting a sample of biological tissue. In this embodiment, the shell resembles a lozenge, but in practice there is not limitation to the shape of the shell. The pivotable functionality of the pair of jaws acts to enable the jaws to move apart to form an entrance to the volume that faces towards the distal end of the jaw assembly (see FIG. 8B). Each of the pair of jaws 312a, 312b comprises an electrically conductive outer shell (e.g. made of metal, such as copper, silver, gold or aluminium). In one example, the electrically conductive outer shell is formed from stainless steel with an silver or gold plating on its outer surface. The inner stainless steel layer has a lower thermal conductivity than the outer plating, which improves the thermal barrier between the internal volume and the outer surface to ensure that the tissue sample does not become damaged due to being heated. In the embodiment illustrated in FIG. 8A, each of the pair of jaws 312a, 312b comprises a thin layer of thermal insulation 318. This layer may be made from a material having a low thermal conductivity. For example, a plastic material such as polystyrene may be used. The layer of thermal insulation 318 may be formed (e.g. bonded or otherwise secured) to an inner surface of the corresponding electrically conductive outer shell. Alternatively, the layer of thermal insulation may be moulded first and have a layer of metallisation or plating formed thereon to provide the electrically conductive shell. In this embodiment, each of the pair of jaws 312a, 312b form open cup-like structures which oppose one another at their open edges. The opposing edges 316 of the pair of jaws 312a, 312b may have a serrated or saw-tooth profile. The opposing edges 316 are arranged to mate (i.e. fit together) when the jaw assembly is in the closed configuration. There may be a groove along the edges to ensure that fields are present inside the jaws, i.e. this would form an EM gasket or seal to prevent microwave fields entering the tissue contained therein, which may lead to tissue heating. The electrically conductive outer shells are electrically connected in the closed configuration. This means that the shell of conductive material may act as a Faraday cage to prevent or inhibit electric fields (specifically a microwave field from the energy supplied from the coaxial cable) from existing within the enclosed volume when the distal jaw assembly is closed.

In order to prevent electric fields from penetrating through the electrically conductive outer shell of the pair of jaws 312a, 312b, the electrically conductive material that forms these shells has a thickness of at least three skin depths of the material at the frequency of the microwave energy that is conveyed by the coaxial cable, ideally, this will be five skin depths or more.

The electrically conductive outer shells of the pair of jaws 312a, 312b are electrically connected to the inner conductor 306 of the coaxial cable 304, e.g. via a connection that extends through the hinge 314.

The distal jaw assembly 300 further comprises a sliding sleeve 320 which is movable axially with respect to the coaxial cable 304 to change the distal jaw assembly 300 between closed and open configurations. The sliding sleeve 320 is mounted around the coaxial cable 304 and within the instrument cord 120. In an alternative embodiment, the sleeve may be part of the feed cable itself, i.e. the feed cable may be retractable with respect to the coaxial cable within it. A proximal end of the sliding sleeve is connected to a push rod 322, which extends proximally through the instrument cord and is controllable by the pull trigger 110 discussed above.

The outer sleeve 320 comprises an outer electrically conductive layer and an inner dielectric layer 324. The inner dielectric layer 324 abuts the outer surface of the pair of jaws 312a, 312b and electrically insulates them from the outer electrically conductive layer. The outer electrically conductive layer is electrically connected to the outer conductor 308 of the coaxial cable 304 by a connecting portion 326 that extends through the inner dielectric layer 324 in a region spatially separated from the pair of jaws 312a, 312b.

In this embodiment, the pair of jaws 312a, 312b are biased away from each other, e.g. by including a spring in the hinge 314, so that they are urged against the sliding sleeve 320. Thus, when the sliding sleeve is slid in a proximal direction relative to the pair of jaws 312a, 312b (to the left in FIG. 8A), the pair of jaws 312a, 312b protrudes from the sleeve and opens to provide access to the enclosed volume under the effect of the biasing force. The nature of the movement is controlled by providing a suitable outer profile to the outer shells of the pair of jaws 312a, 312b.

FIG. 8B shows a schematic representation of the distal jaw assembly shown in FIG. 8A when in an open configuration, i.e. when the sleeve 320 has been slid proximally to expose the pair of jaws 312a, 312b. The pair of jaws 212a, 212b are thus open to receive a sample of biological tissue.

In use, the device is inserted into a treatment (sample extraction) location while in the closed configuration. Once in position, the sleeve 220 may be retracted to open the pair of jaws 212a, 212b. When the open jaws are position against a desired portion of tissue, the sleeve 320 is pushed distally over the jaws, which thus grasp and remove a sample of the biological tissue. The opposing edges of the pair of jaws 312a, 312b may be sharpened to improve the effectiveness of the cut. Once the tissue sample is removed and enclosed within the shell of the jaws, microwave energy is supplied through the coaxial cable to coagulate the bleeding surface that remains after the sample is removed. The microwave field emitted by the outer conductive layer of the sleeve and the pair of jaws is discussed in more detail below. Since the closed jaws act as a Faraday cage and the depth of penetration of the microwave field is negligible compared with the thickness of the shell, the sample is protected from the microwave field and therefore unwanted tissue effects are avoided.

A temperature sensor 328 (e.g. a miniature thermocouple or the like) may be mounted inside the enclosed volume to monitor the temperature of the tissue sample. The temperature sensor 328 may be connected to an external processor by a wire 330, which may run through the hinge 314 and along the inside of the feed cable. Temperature sensors may also be connected to the outer jaws or the shell to measure the temperature of the tissue when microwave coagulation or ablation is required.

Early diagnosis and treatment are crucial to surviving lung cancer. The instrument configurations described above are for use with a minimally-invasive ENB procedure for the detection and diagnosis of early-stage lung cancer. However, the delivery of microwaves through such a small cable is intrinsically lossy. In the invention, this problem is addressed by designing the energy delivery cable (in particular within the instrument cord) to limit losses to 2 dB/m when delivering the microwave energy (e.g. at 5.8 GHz).

The cable for delivering the microwave radiation to the target site should be low-loss, have a small cross-section and be flexible. The cable should be low loss to avoid heating during treatment and so that there is enough power at the distal end to produce the desired radiation from the antenna.

A preferred cable type is a coaxial cable which is made up of an inner conductor axially surrounded by a dielectric sheath which is in turn axially surrounded by an outer conductor. The radiating portion in an antenna produced from such a cable may be made up of a section of inner conductor and dielectric sheath which protrudes from the end of the outer conductor of the coaxial cable.

Nevertheless, even with a low loss cable, it is recognised that the power available for ablation at the distal antenna will be limited. To address this, and enable repeatable and consistent ablation to be performed, the instruments discussed above can be used with delivering a combination of RF and microwave energy.

The antennas discussed above can be used to initially deliver RF energy. RF energy can effectively ablate tissue at normal (i.e. relatively low) tissue impedances. An advantage of using RF energy at the beginning of the ablation procedure is that there is virtually no adverse effects due to energy losses. The RF energy causes a negligible amount of cable heating. During this initial phase, while the tissue impedance is low, the instruments above may deliver RF energy to create an ablation sphere around the distal tip with an ablation zone of around 5 mm radius.

As ablation proceeds, the tissue impedance rises and the RF energy becomes less effective. At this stage, microwave energy can still be effective in performing tissue ablation. Accordingly, the energy delivery profile may include microwave energy so that the ablation zone can continue to grow as tissue impedance changes. In general, however, the energy delivery profiles used herein seek to maximise the amount of ablation that can be achieved by the RF energy without the losses associated with delivering microwave energy.

There are a number of ways in which the energy delivery profile can be adapted to include microwave energy. However, since it is the microwave energy that can cause the adverse effects due to losses, it is desirable to incorporate the microwave energy into the energy delivery profile in a manner that minimises the energy loss.

In one example, the tissue impedance may be measured and the microwave energy may be switched in after it is detected that the tissue impedance has exceeded some threshold.

It may not be necessary to detect tissue impedance. For example, in some embodiments, the RF and microwave energy can be delivered in a predetermined time-based profile. In a simple example, the RF energy may be delivered for an initial period (e.g. 1 to 5 minutes), followed by a present period of microwave energy delivery to increase the ablation size.

In the examples above, when the microwave energy is delivered, it may be done in a manner that mitigates the effect of the energy loss. For example, cooling fluid may also be delivered through the instrument cord or in an outer cooling jacket. Alternatively or additionally, the microwave energy may be pulsed, i.e. delivered in preset windows (or ON periods) separated by windows in which no microwave energy is delivered (OFF periods). Having the OFF periods provides some recovery time for energy that is lost along the cable to dissipate. In another example, the microwave energy can be delivered with a duty cycle of 9%, e.g. a 110 ms period consisting of a 10 ms ON portion and a 100 ms OFF portion. The duty cycle may be less than 9%, e.g. 5%.

In order to maintain the ablation effect during the OFF periods, the instrument may be arranged to deliver RF energy during the OFF periods. In other words, the RF and microwave energy may be interleaved. In some embodiments, the RF energy may be applied continuously while the microwave energy is pulsed.

The microwave energy may be delivered at different power levels. For example, one microwave energy delivery profile may comprises an initial ON period of 2 seconds at 100 W, followed by a subsequent ON period of 100 seconds at 10 W. This profile delivers 1200 J into the system in a front-loaded manner. The total energy delivered may affect the ablation zone size. In another example, 370 J may be delivered using a similar front-loaded profile, e.g. comprising an initial ON period of 5 seconds at 10 W, followed by a subsequent ON period of 80 seconds at 4 W.

In another example, the microwave energy may be modulated at the frequency of the RF energy, i.e. the amplitude of the microwave field may vary in time. This may enable the effects of the RF and microwave fields to be combined.

Other considerations for reducing loss and cable heating may involve adapting the physical characteristics of the instrument. For example, the coaxial cable used for energy delivery may be customised to have a characteristic impedance better suited for low loss energy delivery. The antenna may configured to limit reflected power, or may be provided with chokes to prevent sheath currents. However, such customisations may not be an economical way of realised the reduction in energy loss required.

The invention claimed is:

1. An electrosurgical apparatus for delivering radiofrequency (RF) and microwave energy into lung tissue, the electrosurgical apparatus comprising:
   a generator for generating the RF and microwave energy separately or simultaneously;
   an electromagnetic navigation bronchoscope having a steerable instrument cord for non-percutaneous insertion into a patient's lungs, the instrument cord having an instrument channel running along its length;

an electrosurgical instrument comprising:
- a coaxial cable connected to the generator and arranged to convey the RF and microwave energy, the coaxial cable having an inner conductor, an outer conductor, and a dielectric material separating the inner conductor and outer conductor; and
- a radiating tip portion disposed at a distal end of the coaxial cable to receive the RF and microwave energy from the coaxial cable, wherein the radiating tip portion comprise a first conductive element electrically connected to the inner conductor and a second conductive element electrically isolated from the inner conductor, wherein the first conductive element and the second conductive element are arranged to act as:
- an active electrode and a return electrode for delivering the RF energy into tissue surrounding the radiating tip portion, and
- an antenna for radiating the microwave energy as a localized microwave field, wherein the electrosurgical instrument is insertable through the instrument channel, of the steerable instrument cord in the electromagnetic navigation bronchoscope, wherein the radiating tip portion includes radiating slots which are separated by coaxial sections, the first conductive element comprising the inner conductor of the coaxial cable, the second conductive element comprising the outer conductor of the coaxial cable, the coaxial sections including the first conductive element and the second conductive element, the radiating slots including the first conductive element, the first conductive element being surrounded along its length by the dielectric material, and the dielectric material of the coaxial cable being exposed with the radiating slots, and wherein the plurality of radiating slots include a proximal slot having a length of about one tenth of a wavelength of the microwave energy in the dielectric material, a distal slot having a length of about one tenth of the wavelength of the microwave energy in the dielectric material, and an intermediate slot between the proximal slot and the distal slot, the intermediate slot having a length of about one quarter of the wavelength of the microwave energy in the dielectric material.

2. The electrosurgical apparatus according to claim 1, wherein the coaxial cable and the radiating tip portion both have a maximum outer diameter equal to or less than 1.9 mm.

3. The electrosurgical apparatus according to claim 1, wherein the coaxial cable is arranged to exhibit a loss of 2 dB/m or less when conveying the microwave energy.

4. The electrosurgical apparatus according to claim 1, wherein the generator is arranged to deliver the RF and microwave energy to cause tissue ablation at the radiating tip portion according to an energy delivery profile.

5. The electrosurgical apparatus according to claim 4, wherein the generator is configured to deliver the energy delivery profile, and wherein the energy delivery profile comprises an initial portion consisting solely of the RF.

6. The electrosurgical apparatus according to claim 4, wherein the generator is configured to deliver the energy delivery profile, and wherein the energy delivery profile comprises a portion in which the microwave energy is delivered, the generator being arranged to modulate the microwave energy at a frequency corresponding to the RF energy.

7. The electrosurgical apparatus according to claim 4, wherein the generator is configured to deliver the energy delivery profile, and wherein the energy delivery profile comprises a microwave ablation portion comprising the microwave energy as pulsed microwave energy.

8. The electrosurgical apparatus according to claim 7, wherein the pulsed microwave energy comprises a series of ON portions in which the microwave energy is delivered separated by a series of OFF portions where the microwave energy is not delivered, and wherein the RF is delivered in one or more of the OFF portions.

9. The electrosurgical apparatus according to claim 4, wherein the generator is arranged to detect an impedance of the lung tissue at the radiating tip portion, and wherein the generator is configured to adjust the energy delivery profile based on the detected impedance.

10. The electrosurgical apparatus according to claim 9, wherein the generator is configured to deliver the energy delivery profile, and wherein the energy delivery profile comprises a first portion consisting solely of the RF followed by a second portion comprising the microwave energy, and wherein the generator is arranged to switch to the second portion when the tissue impedance is determined to exceed a predetermined threshold.

11. The electrosurgical apparatus according to claim 1, wherein the first conductive element and the second conductive element both extend to a distal face of the radiating tip portion.

12. The electrosurgical apparatus according to claim 1, wherein the inner conductor of the coaxial cable is exposed at the distal face of the radiating tip portion.

13. An electrosurgical apparatus for delivering radiofrequency (RF) and microwave energy into lung tissue, the electrosurgical apparatus comprising:
- a generator for generating the RF and microwave energy separately or simultaneously;
- an electromagnetic navigation bronchoscope having a steerable instrument cord for non-percutaneous insertion into a patient's lungs, the instrument cord having an instrument channel running along its length;
- an electrosurgical instrument comprising:
  - a coaxial cable connected to the generator and arranged to convey the RF and microwave energy, the coaxial cable having an inner conductor, an outer conductor, and a dielectric material separating the inner conductor and outer conductor; and
  - a radiating tip portion disposed at a distal end of the coaxial cable to receive the RF and microwave energy from the coaxial cable, wherein the radiating tip portion comprises a first conductive element electrically connected to the inner conductor and a second conductive element electrically isolated from the inner conductor, wherein the first conductive element further comprises a length of the inner conductor that extends beyond a distal end of the outer conductor, the first conductive element being surrounded along its length by the dielectric material, wherein the first conductive element and the second conductive element are arranged to act as:
- an active electrode and a return electrode for delivering the RF into tissue surrounding the radiating tip portion, and an antenna for radiating the microwave energy as a localized microwave field, wherein the electrosurgical instrument is insertable through the instrument channel of the steerable instrument cord in the electromagnetic navigation bronchoscope, wherein the radiating tip portion includes radiating slots which are separated by coaxial sections, the second conductive element comprising the outer conductor of the coaxial cable, the coaxial sections including the first conductive element and the second conductive element, the radiating slots including the first conductive element, and the dielectric material of the coaxial cable being exposed with the radiating slots, and wherein the plurality of radiating slots include a proximal slot having a length of about one tenth of a wavelength of the microwave energy in the dielectric material, a distal slot having a length of about one tenth of the wavelength of the microwave energy in the dielectric material, and an intermediate slot between the proximal slot and the distal slot, the intermediate slot having a length of about one quarter of the wavelength of the microwave energy in the dielectric material.

\* \* \* \* \*